United States Patent
Seidman

(10) Patent No.: US 8,244,083 B2
(45) Date of Patent: Aug. 14, 2012

(54) STEERABLE, THIN FAR-FIELD ELECTROMAGNETIC BEAM

(76) Inventor: Abraham N. Seidman, Los Angeles, CA (US)

( * ) Notice: Subject to any disclaimer, the term of this patent is extended or adjusted under 35 U.S.C. 154(b) by 641 days.

(21) Appl. No.: 12/284,034

(22) Filed: Sep. 17, 2008

(65) Prior Publication Data

US 2010/0067842 A1    Mar. 18, 2010

Related U.S. Application Data

(60) Provisional application No. 60/994,112, filed on Sep. 17, 2007.

(51) Int. Cl.
*G02B 6/26* (2006.01)
*G02B 6/32* (2006.01)

(52) U.S. Cl. ............................. 385/34; 385/31
(58) Field of Classification Search ........... 385/31, 385/34
See application file for complete search history.

(56) References Cited

U.S. PATENT DOCUMENTS

| | | | | |
|---|---|---|---|---|
| 4,389,593 A * | 6/1983 | DeSantis et al. | ............ | 315/4 |
| 4,553,068 A * | 11/1985 | Brandt | ............ | 315/4 |
| 4,727,551 A * | 2/1988 | Scharlemann | ............ | 372/2 |
| 5,309,411 A * | 5/1994 | Huang et al. | ............ | 367/140 |
| 5,327,139 A * | 7/1994 | Johnson | ............ | 342/22 |
| 5,331,445 A * | 7/1994 | Dickson et al. | ............ | 359/15 |
| 5,371,347 A * | 12/1994 | Plesko | ............ | 235/462.15 |
| 5,519,198 A * | 5/1996 | Plesko | ............ | 235/462.4 |
| 5,659,561 A * | 8/1997 | Torruellas et al. | ............ | 372/22 |
| 5,778,133 A * | 7/1998 | Plesko | ............ | 385/146 |
| 5,864,128 A * | 1/1999 | Plesko | ............ | 235/462.35 |
| 5,886,332 A * | 3/1999 | Plesko | ............ | 235/472.01 |
| 5,943,161 A * | 8/1999 | Shinozaki et al. | ............ | 359/330 |
| 5,963,359 A * | 10/1999 | Shinozaki et al. | ............ | 359/326 |
| 6,052,213 A * | 4/2000 | Burt et al. | ............ | 359/237 |
| 2008/0024873 A1 * | 1/2008 | Kim et al. | ............ | 359/642 |
| 2009/0303154 A1 * | 12/2009 | Grbic et al. | ............ | 343/909 |

* cited by examiner

*Primary Examiner* — K. Cyrus Kianni
(74) *Attorney, Agent, or Firm* — A. N. Seidman

(57) ABSTRACT

A method and apparatus for forming and controlling a microwave Bessel beam which may be utilized for examining microstructure including very early stage tumors.

10 Claims, 5 Drawing Sheets

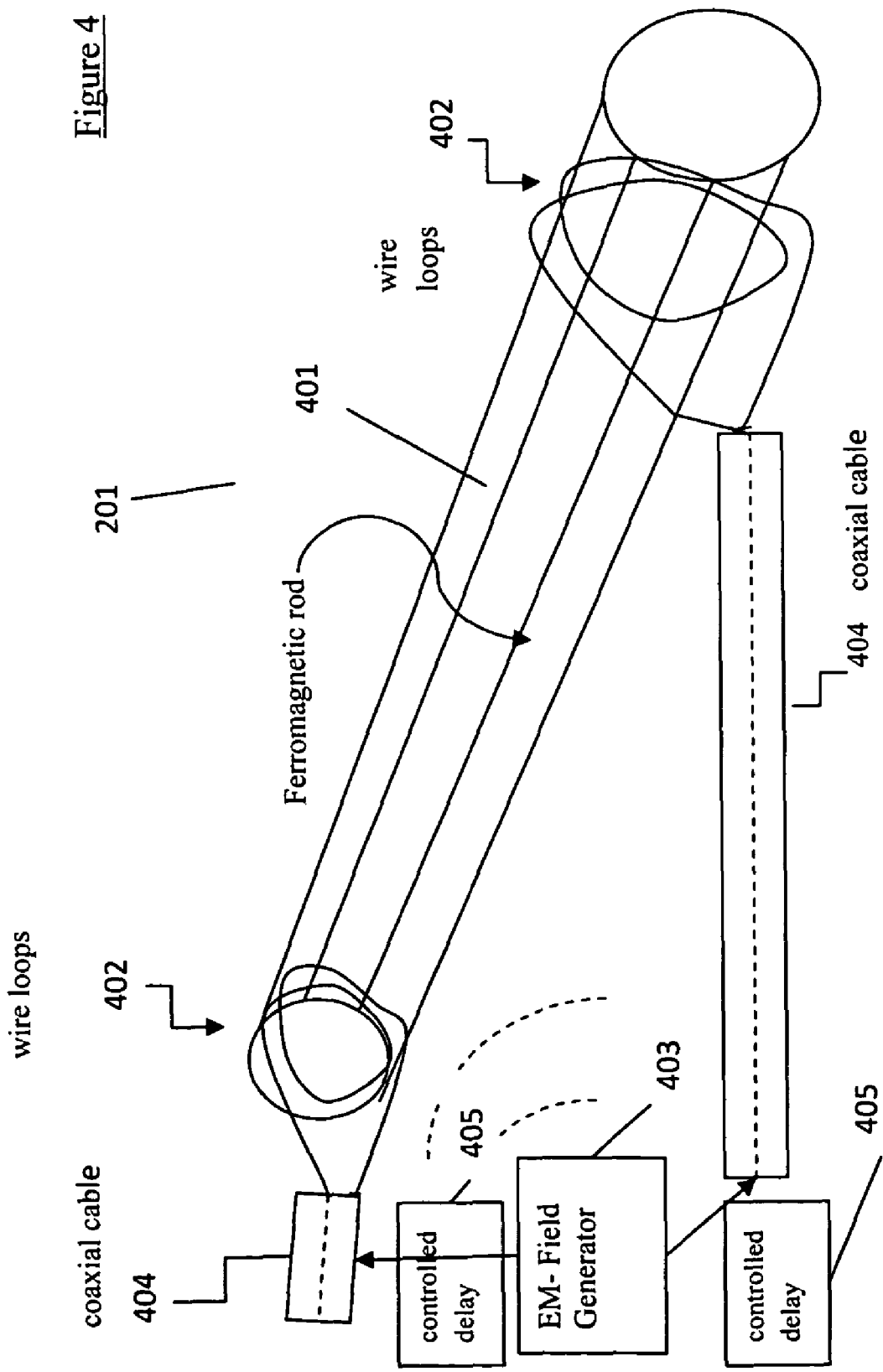

STEERABLE, THIN FAR-FIELD ELECTROMAGNETIC BEAM

This application claims the benefit of provisional application 60/994,112 filed 17 Sep., 2007 (entitled: "STEERABLE, THIN FAR-FIELD ELECTROMAGNETIC BEAM").

FIELD OF THE INVENTION

This invention relates to steerable thin penetrating electromagnetic beams utilizing photonic crystals or meta-materials.

This invention relates to detection and identification of microstructures by penetrating electromagnetic radiation of a relatively long wavelength.

BACKGROUND

References made throughout this specification are grouped together below. Reference is cited by author [Number], e.g. Aruga [1]:
1. Aruga, T., 1997, "Generation of long-range nondiffracting narrow light beams," Appl. Opt., Vol. 36, 3762-3768 (1997).
2. Aruga, T., S. W. Li, 1999, "Super high resolution for long-range imaging," Appl. Opt. Vol. 38, 2795-2799.
3. Aydin, K., I. Bulu, E. Ozbay, 2005, "Focusing of electromagnetic waves by a lefthanded metamaterial flat lens," 31 Oct. 2005/Vol. 13, No. 22/OPTICS EXPRESS 8753
4. Belov, P. A., M. G. Silveirinha, 2006a, "Resolution of sub-wavelength transmission devices formed by a wire medium, Phys. Rev. B 73, 033108 (2006), arXiv: cond-mat/0610558v1
5. Belov, P. A., Y. Zhao, S. Sudhakaran, A. Alomainy, Y. Hao, 2006b, arXiv:cond-mat/0610558v1 19 Oct. 2006
6. Cubukcu, E., K. Aydin, E. Ozbay, S. Foteinopoulou, and C. M. Soukoulis, 2003a, "Electromagnetic waves: Negative refraction by photonic crystals," Nature 423, 604 (2003).
7. Cubukcu, E., K. Aydin, S. Foteinopolou, C. M. Soukoulis, and E. Ozbay, 2003b, "Subwavelength resolution in a two-dimensional photonic crystal based superlens," Phys. Rev. Lett. 91, 207401 (2003).
8. Dolling, G., M. Wegener, C. M. Soukoulis, S. Linden (2007) Vol. 32 pp. 53-55, Optics Letters "Negative-index metamaterial at 780 nm."
9. Dolling, G., C. Enkrich, M. Wegener, C. M. Soukoulis, S. Linden, (2006a) Science, Vol. 312, p. 892
10. Dolling, G., C. Enkrich, M. Wegener, C. M. Soukoulis, S. Linden, (2006b) Opt. Lett., Vol 31, p. 1800
11. Durnin, J. 1987, "Exact solution for nondiffracting beams I: the scalar theory," J. Opt. Soc. Am. A Vol 9, pp. 651-654 (1987).
12. Durnin, J. Miceli, Jr., J. H. Eberly, "Diffraction-free beams," Phys. Rev. Lett., Vol. 58, 1499-1501 (1987).
13. Z. Jiang, Q. Lu, and Z. Liu, "Propagation of apertured Bessel beams," Appl. Opt. 34, 7183-(1995)
14. Luo, C., S. G. Johnson, J. D. Joannopoulos, and J. B. Pendry, 2002, "All-angle negative refraction without negative effective index" Phys. Rev. B 65, 201104(R) (2002).
15. Notomi, M., 2000, "Theory of light propagation in strongly modulated photonic crystals: Refraction like behavior in the vicinity of the photonic band gap," Phys. Rev. B 62, 10696 (2000).
16. Parimi, P. V., W. T. Lu, P. Vodo, and S. Sridhar, 2003, "Imaging by flat lens using negative refraction," Nature 426, 404 (2003).
17. Pendry, J. B., A. J. Holden and W. J. Stewart I. Youngs, (1996) Extremely Low Frequency Plasmons in Metallic Mesostructures, Vol. 76, Number 25, Physical Review Letters, 17 Jun. 1996.
18. Pendry, J. B., A. J. Holden, D. J. Robbins, and W. J. Stewart, (1999) "Magnetism from Conductors and Enhanced Nonlinear Phenomena," IEEE Transactions on Microwave Theory and Techniques, vol. 47, no. 11, November (1999). 2075.
19. Pendry, J. B., (2000) "Negative Refraction Makes a Perfect Lens," Phys. Rev. Lett. 85, 3966 (2000).
20. Pendry, J. B., D. Schurig, D. R. Smith, 2006, "Controlling Electromagnetic Fields," Science, Vol. 312, pp. 1780-1782.
21. Pimenov, A., Loidl, K. Gehrke, V. Moshnyaga, K. Samwer, 2007, "Negative Refraction Observed in a Metallic Ferromagnet in the Gigahertz Frequency Range, Physical Review Letters, Vol. 98, p. 197401 (2007).
22. Shalaev, V. M., W. CAI, U. K. Chettiar, H.-K. Yuan, A. K. Sarychev, V. P. Drachev, and A. V. Kildishev, (2005) "Negative index of refraction in optical metamaterials," Opt. Lett. 30, 3356-3358 (2005).
23. Shelby, R. A., D. R. Smith, and S. Schultz: Experimental Verification of a Negative Index of Refraction" Science 292, 77-70 (2001).
24. Smith, D. R. S. Schultz, P. Marcos, and C. M. Soukoulis, "Determination of effective permittivity and permeability of metamaterials from reflection and transmission coefficients., Phys. Rev. B65, 195104 (2002)
25. Synge E H, 1928, A suggested method for extending microscopic resolution into the ultra-microscopic region. Phil Mag 6, 356-362 (1928)
26. Uday K. Chettiar, Alexander V. Kildishev, Thomas A. Klar†, and Vladimir M. Shalaev, "Negative index metamaterial combining magnetic resonators with metal films"
27. Veselago, V., G., 1968, "The electrodynamics of substances with simultaneously negative values of $\in$ and μ." Soviet Physics USPEKI 10, 509-514
28. Wiley, B. J., Y. Chen, J. McLellan, Y. Xiong, Z-Y Li, D. Ginger, Y. Xia, 2007, "Synthesis and Optical Properties of Silver Nanobars and Nanorice," Nano Letters, Vol. 0, No. 0, A-E, American Chemical Society, Published on Web Mar. 8, 2007
29. Zhang, S., W. Fan, N. C. Panoiu, K. J. Malloy, R. M. Osgood and S. R. J. Brueck, 2005, "Demonstration of Near-Infrared Negative Index Metamaterials," Phy. Rev. Lett. 95, 137404.
30. Zhang, S., W. Fan, N. C. Panoiu, K. J. Malloy, R. M. Osgood and S. R. J. Brueck, 2006, "Optical negative-index bulk metamaterials consisting of 2D perforated metal-dielectric stacks
31. Zhao, Y., P. A. Belov, Y. Hao, 2006, "Spatially dispersive finite-difference time-domain analysis of sub-wave-length imaging by the wire medium slabs," arXiv: physics/06605025v1 3 May 2006.

Microstructures such as cancer cells have as lower limit the cells of their normal matrix (e.g., breast tissue). Brain neuron axons have characteristic diameters of 8 μm to 80 μm. Animal virus dimensions range from poliomyletis (30 nm) to vaccinia (230 nm). Originally Koch and Pasteur, in the second half of the 18th century studied certain microstructures (e.g., anthrax) with electromagnetic means, namely light, in the visible wavelength range about 200 nm-800 nm (i.e., 2000-8000 Å). The difficulty with applying these wavelengths is that they only detect the presence of microstructure (e.g., cancer cells from a biopsy or, anthrax spores on the surface of a letter or package), within the limits of the penetrability of visible light, e.g. on or near surface locations.

Probing into structures is easier using a relatively longer wavelength. Such electromagnetic radiation (e.g., millimeter or centimeter wavelength microwaves) will penetrate letters and packages.

One difficulty, however, with longer wavelengths is the mismatch with the size of the objects they are trying to detect. The ordinary limit of smallest features detectable by electromagnetic wavelength $\lambda$ is approximately of the order of that wavelength, $\lambda$. The Abbe-Rayleigh theory (Born and Wolf, $2^{nd}$ edition, p. 333 ff, p. 420 ff) expresses the discernable dimension separation between two interfering electromagnetic radiation waves as $\lambda$ with some additional numerical factors of the order of unity which may depend upon the coherence of the light and on the geometry of the object for which the dimensional resolution is sought.

The near field effect of using small apertures, i.e., $\lambda \gg a$, where a is the aperture radius, have been successfully used to increase resolution beyond the Abbe-Rayleigh limit. Ash and Nicholls, for the near field, (Nature, 237, pp. 510-512, 1972) demonstrated a spatial resolution of several millimeters at $\lambda=3$ cm using a 1.5 mm diameter circular aperture in a conducting screen. Golosovsky and Davidov, (Appl. Phy Lett., 68 (11), 1996, pp. 1579-1581) also used the near-field for microwave imaging. In contrast to Ash and Nicholls, however, they used a narrow resonant slit (instead of a circular aperture) to achieve a high transmission coefficient (in a limited frequency range) compared to the circular aperture. They were able to get a resolution of 70 µm-to 100 µm at 80 GHz ($\lambda=3.75$ mm). The resolution was therefore about $\lambda/50$. Knoll and Keilmann (Nature, 399, pp. 134-137, 1999) used an antenna tip to act as a scattering center. The investigation was done in the infrared and achieved a near-field resolution of 100 nanometers, about $\lambda/100$. A scattering tip was actually used in place of an aperture.

First attempts to initiate confined beams ran up against energy conservation. Basically, a beam on some enclosing spherical surface at radius $R_1$ intersects the sphere of $R_1$ with a finite area of $\pi \in^2$, where $\in$ is the radius of the small spot illuminated on the interior surface of the enclosing sphere with radius $R_1$. For a constant energy source, the energy density of the spot on an enclosing sphere of $R_2$ is $(R_1/R_2)^2 \pi \in^2$, where $R_2 \gg R_1$. The only way to soup-up the energy density is to supply more energy to the beam. As $R_2$ goes toward infinity, an infinite amount of energy would have to be confined by the beam.

However, Durbin (1987), Durnin, et al. (1987), however, found that a beam with a considerable depth of field could effectively be confined in radial direction. These are typically referred to as "Bessel beams", or "quasi-non-diffracting beams" or similar.

As a more simple construction, photonic crystals showed a band structure with a negative dispersion which gave rise to an effective negative index of refraction. See, for example, Aydin and Bulu (2005), Luo (2002) Notomi (2000), E. Cubukcu (2003a, 2003b), and Parimi (2003). Typical photonic crystals are composed of a three dimensional array of metal or dielectric wires/tubes which are arranged with symmetry in two dimensions, the third dimension being the axis parallel to the (finite) lengths of wires.

As another example, Aruga (1997), Aruga, et al. (1999), showed a "long-range non-diffracting" beam with a 10 cm diameter telescope at 1 km, with an improvement over diffraction-limited optics: measured by: (width of ordinary Bessel beam)/(width of ordinary beam)=0.72. Aruga used a telescope objective with a spherical aberration to produce the Bessel beam.

Magnetic resonance imaging with a minimum resolution around 0.1 to 0.01 mm has been used to visualize the structure of a brain, before surgery on that brain. The brain may change shape after an incision because the pressure of the spinal-cephalic fluid may change. There are also other naturally occurring movements of the brain with time. While a patient may have additional magnetic resonance scanning done during the surgery, the results are not simultaneous with the surgery and often may be difficult to perform during a hiatus in the brain surgery.

One aspect in achieving a diagnostic/treatment tool/method/apparatus is to produce a "narrow," i.e., a beam elongated in its direction of propagation (e.g., "z"), while limited in it other dimensions, for example in the other two dimensions ("x" and "y," for a Cartesian coordinate system).

As an aid in better defining a beam, an apodizer may be utilized. (Jiang, et al., 1995).

An additional requirement exists for the practical utilization of a diagnostic/treatment apparatus, namely, the steerability of the beam.

In an MRI, for example, a patient may be moved repeatably into and out of a magnetic field scanning region, or, as in a CAT (computer aided tomography) scan, a scanning X-ray unit may mechanically progressively revolve around and along a patient.

While it is possible to mechanically move the beam, or the subject of the inspection, a better solution is to move the beam. A need exists for a system, method and apparatus which can detect cancer cells while there are relatively few of them, and, with additional capability for ablating detected cancer cells. A pertinent element in such an apparatus may be an electronically steerable narrow beam.

Metamaterial is defined, for example, in reference 20, [Controlling Electromagnetic Fields, J. B. Pendry, D. Schurig, D. R. Smith, *Science* 312, 1780 (2006)]: "A new class of electromagnetic materials (1, 2) is currently under study: metamaterials, which owe their properties to Subwavelength details of structure rather than to their chemical composition, can be designed to have properties difficult or impossible to find in nature."

SUMMARY OF THE INVENTION

In the steerable "beam former" an additional magnetic field is applied to the elements of the beam former (in a "two-dimensional" photonic crystal formed from rods, the magnetic field is applied by sourcing a controlled current through a conduit spirally encircling a portion of a "control rod", which may be ferromagnetic where the magnetic field can be controlled in frequency, amplitude and phase, rod by rod, or collectively for all of the control rods, which may form a subset of all of the rods of the "two-dimensional" photonic crystal. The non-control rods of the two-dimensional photonic crystal may also be non-ferromagnetic metal rods or dielectric non-metal rods. The active beam-former may also use "meta-materials" for that part of the beam former that is not made up of the ferromagnetic control rods.

BRIEF DESCRIPTION OF THE DRAWINGS

For a more complete understanding of the present invention, and the advantages thereof, reference is now made to the following descriptions taken in conjunction with the accompanying drawings, in which:

FIG. 2b shows a control source for the beam-former of FIG. 2a;

FIG. 4 shows an exemplary control rod utilizing a signal from an electromagnetic field generator and wire-winding on a ferromagnetic rod or wire such as soft iron.

DETAILED DESCRIPTION OF THE BEST MODES

The following description is of the best mode presently contemplated for carrying out the invention. This description is not to be taken in a limiting sense, but is merely made for the purpose of describing the general principles of the invention. The scope of the invention should be determined with reference to the claims.

Figure 1:
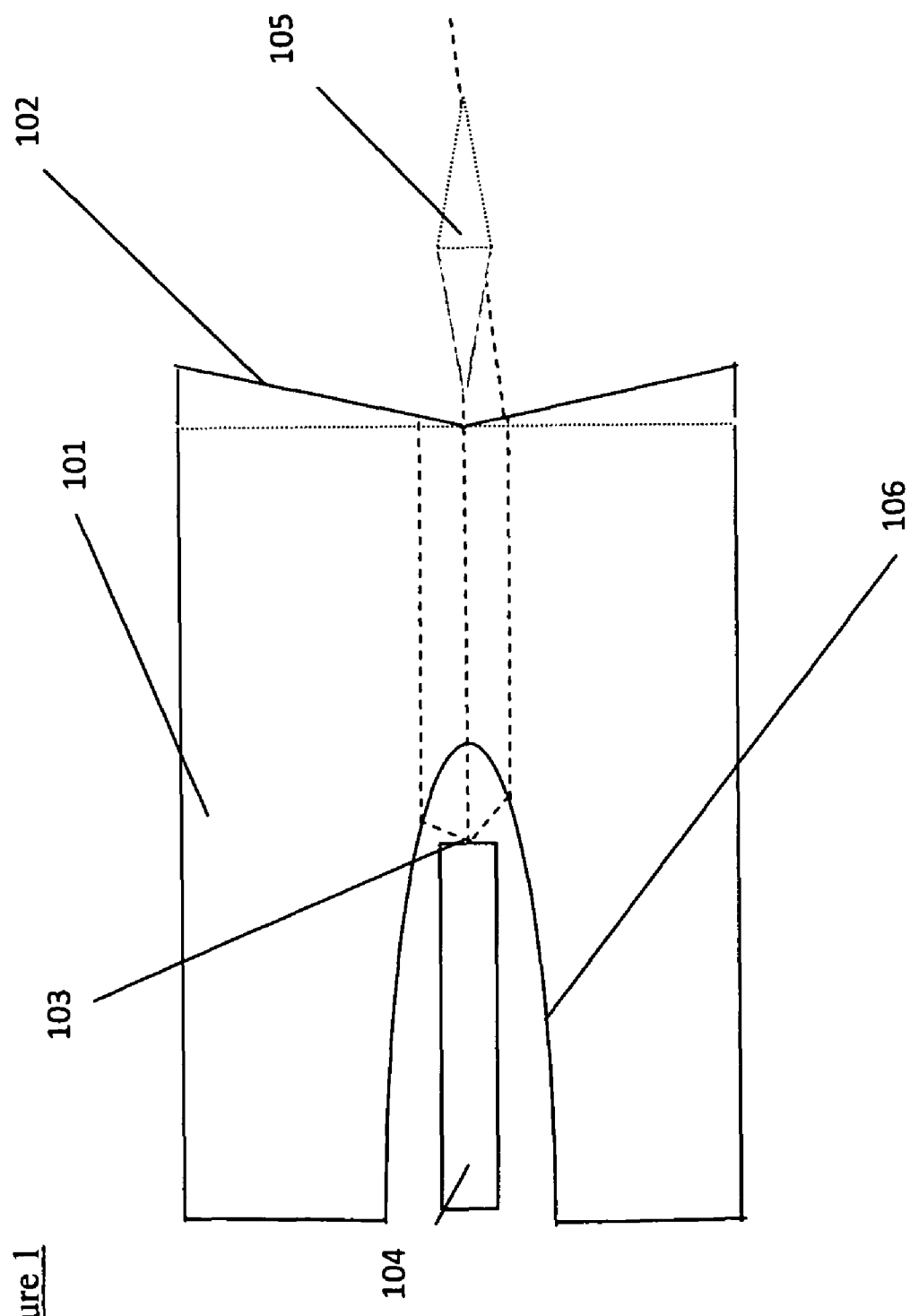
FIG. 1 shows a general layout for a beam-former based on a material with a negative index of refraction; t.

A system such as FIG. 1 includes a quasi-line source 104, an initial beam shaper 101 with a negative index of refraction arranged with an internal parabola 106 to focus (index of refraction being −1) the line at parabola-focus parallel line into a beam in, for example, a Bloch mode "photonic crystal" (PC) composed of parallel metal wires/rods which has end "rods" of ferromagnetic material, such as soft iron cylinders (RODS), 201 (FIG. 2a) which enable the ends of the PC to initiate a "Bessel-beam" with a very long volume of "quasi-non-diffraction."

As shown in FIG. 1, the beam is sourced at a horizontal aperture (descending into the paper, in a two dimensional symmetry of a three-dimensional structure). FIG. 1 shows the "exit walls" 102 for the beam exiting and forming an overlapping region 105 where the Bessel beam volume is maintained. As shown in this FIG. 1, the mechanical focusing action of the exit walls 204 help in the formation of the Bessel beam region. The angles, 204 and 205 of the exit walls are meant to be small for the Bessel beam region 105 to be more elongated. FIG. 1 shows relatively large angles ϕ 204 and θ 205 for illustration purposes. As ϕ 204 and θ 205 become smaller, the Bessel beam region 105 expands. The Bessel beam region 105 is a region of quasi-non-diffraction where the beam maintains its width and does not expand, or expand much, over that region for a considerable distance.

Figure 2A:
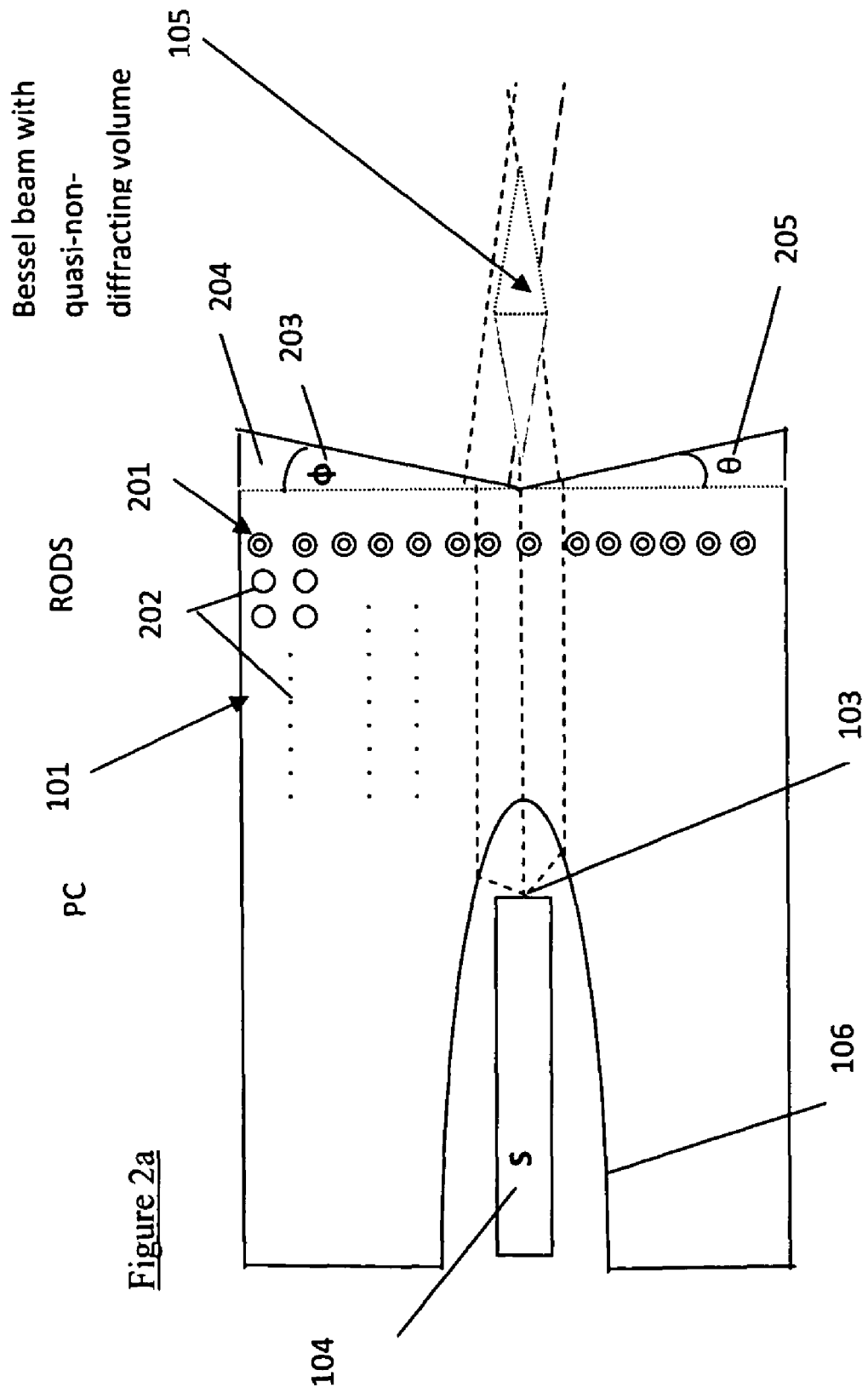
FIG. 2a shows a beam-former utilizing a negative index of refraction photonic crystal and "control rods"

A shown in FIG. 2a, the mechanical walls are replaced or supplemented by the electromagnetically activated and electromagnetically active "control rods" 201. In this exemplary FIG. 2a, the rest of a photonic crystal is shown as other rods 202. Typically these other rods may be made of a dielectric, such as alumina, or a non-ferromagnetic metal, such as aluminum or copper.

The ferromagnetic control cylinders, shown as an illustration as end-cylinders, may also act to steer the beam in response to variable magnetic and electric fields applied to them, where the angles ϕ 204 and θ 205 may not be equal. The differential steering of angles ϕ 204 and θ 205 provides for steering the Bessel beam region electronically in a variable direction.

The basis for the steering from the ferromagnetic rods is derived from Pendry, et al [18]. Starting from the formulation for non-ferromagnetic rods, where the magnetic field H is the sum of the inducing field and the "back-field" arising from the edge effects, where the relative edge effect is, per rod spacing of "a," and the relative area of a rod or radius "r":

(Eq. 8, Pendry, et al. [18])

$$H = H_0 + j\frac{\pi r^2}{a^2} j$$

Then calculating the emf (electromotive force) around a loop around the "rod" of radius "r", since the emf on the closed loop is zero, and solving for the current "j":

(Eq. 10, Pendry, et al. [18])

$$j = \frac{-i\omega\pi r^2 \mu_0 H_0}{i\pi\omega r^2\left[1 - \frac{\pi r^2}{a^2}\right] - 2\pi r\sigma} = \frac{-H_0}{\left[1 - \frac{\pi r^2}{a^2}\right] + i\frac{2r\sigma}{\omega r^2 \mu_0}},$$

Therefore, one can solve for $H_{ave}$:

(Eq. 12, Pendry, et al. [18])

$$H_{AVE} = H_0 - \frac{\pi r^2}{a} j = H_0 - \frac{\pi r^2}{a^2}\frac{-H_0}{\left[1 - \frac{\pi r^2}{a^2}\right] + i\frac{2r\sigma}{\omega r^2 \mu_0}},$$

Then, using the relationship about the bulk or average quantities, one finds:

$$B_{AVE} = \mu_0 H_0 \qquad\qquad \text{(Eq.11, Pendry, et al. [18])}$$

So that an effective permeability is then given as:

(Eq. 13, Pendry, et al. [18])

$$\mu_{eff} = \frac{B_{AVE}}{\mu_0 H_{AVE}}$$

However, in the present invention, the presence of an imposed controlling magnetic field means that in the above equations the ambient magnetic field is no longer $H_0$, rather it is $H_0-H_1$, where $H_1$ represents the controlling magnetic field. Instead of just $H_0$, there is now $H_0-H_1$, where $(\omega_1\mu_1)(\omega_0\mu_0)^{-1}H_1=H_0(\mu_1/\mu_0)(\omega_1/\omega_0)(H_1/H_0)$ and $H_1$ is the field produced electromagnetically by winding the outer ends of the ferromagnetic cylinders with wires connected by coaxial cable, out of phase 180° (π), where the coaxial cable is led from the source field. The phasing can be varied as well as amplitude and frequency. For example, if the frequency of $H_1$ is ½ of $H_0$ the effect on the total amplitude is to decrease the negative effective amplitude component of $H_1$ by ½, so that much control can be exerted by varying the frequency of $H_1$ alone The parameters $\omega_1$ and $H_1$ can be adjusted, where $\mu_1$ may typically range from $10^4$ to $10^6$, for typical common ferromagnetic materials the permeability of the ferromagnetic material, or similar. The phase relationship between $H_0$ and $H_1$ may be set such that the effective permeability of the RODS 201 brings about an effective permeability of $\mu_0=-1$.

FIG. 4 shows an embodiment of an individually controllable (ROD) assembly 201 which has a ferromagnetic rod 401 and wire loops 402. As shown in this embodiment coaxial cables 404 which may include phase adjustment capability (by delay of electromagnetic power/signal. Other known methods for controlled delay 405 of an electromagnetic signal may also be used. The electromagnetic field generator 403 may typically originate the electromagnetic energy which is formed into a Bessel beam, which has coherence into the far-field.

It is important to note that the ferromagnetic cylinders 201 (RODS) may be interspersed in various arrangements with the non-ferromagnetic cylinders 202, or other meta-material, and is not limited to an "end" arrangement. The ferromagnetic cylinders 201 may be set up as more than one cylinder thick 201.

Figure 3:
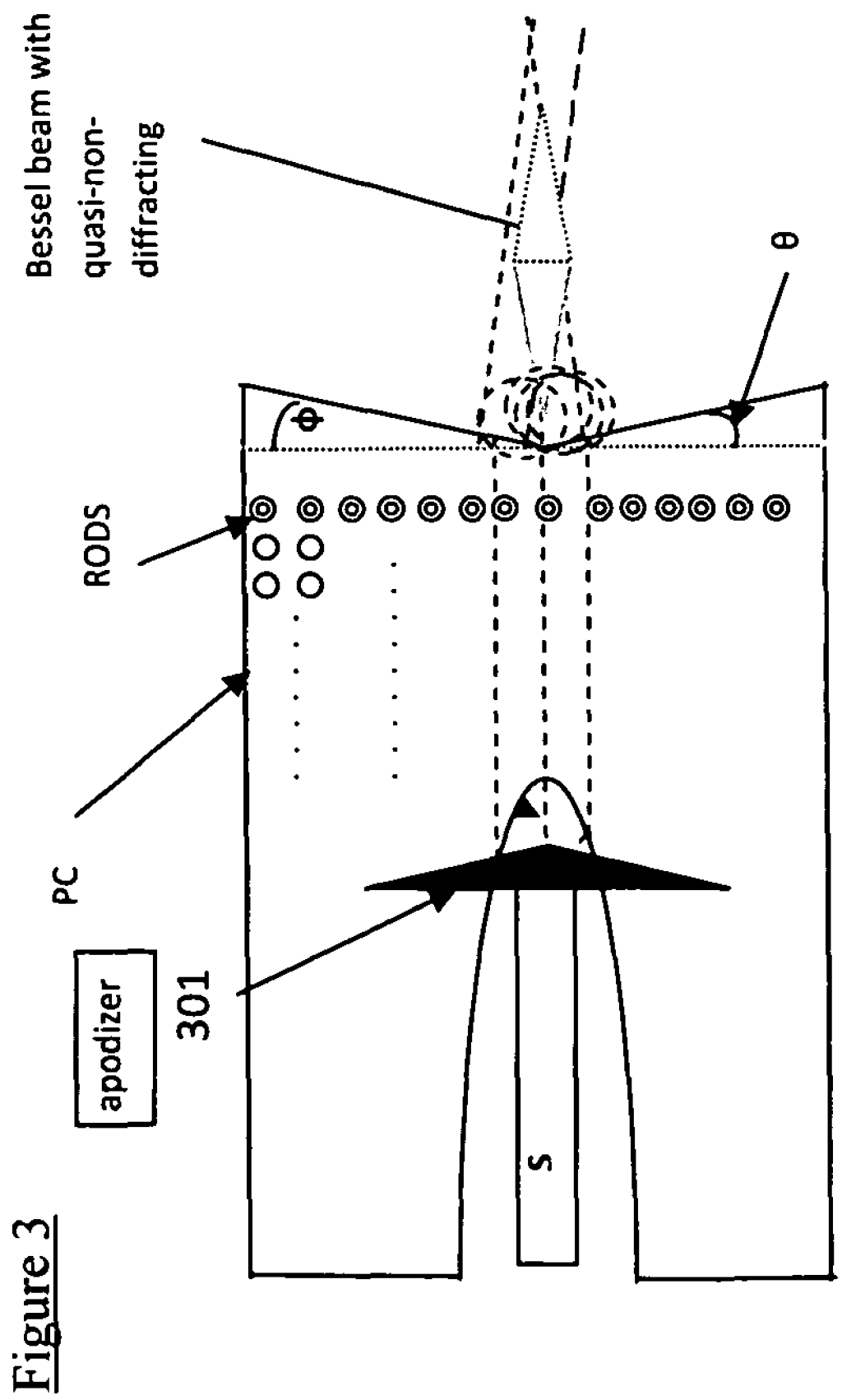
FIG. 3 shows the utilization of an apodizer to further define the beam-former beam.

An apodizer 301 may be included for aperturing the Bessel beam. See FIG. 3.

Figure 2B:
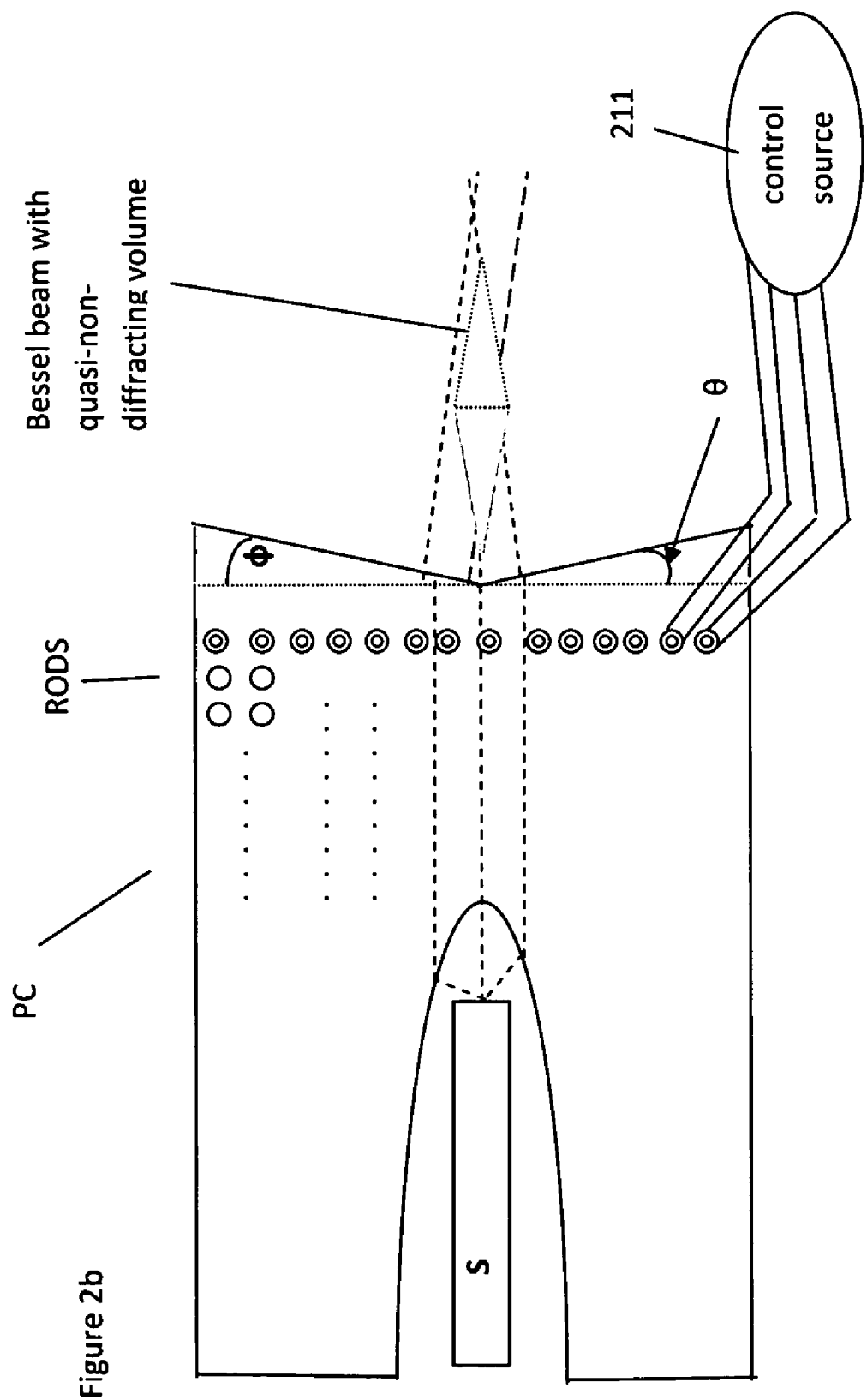

In an embodiment, each rod may be controlled 211 individually. See FIG. 2b.

One point-of-view of the use of negative index of refraction photonic crystals or metamaterials, is that the evanescent waves of (in this case) a line source are captured so that we can use it to produce a very narrow "Bessel beam," in the far field; and then use that fine beam to explore an object of interest in the far field, much as Synge (1928) and others use a near-field "small dot" of illumination to explore relatively (to the beam width) large, close objects in the near field. It should be noted that for positive index of refraction material such as a photonic crystal operating with parameters such that the index of refraction is positive, may be used in a similar manner as the negative index of refraction material, except, for example, that the angles φ 204 and θ 205 of the exit walls 203 (FIG. 2), are such as the exits walls slope back-ward, top and bottom, either mechanically or electromagnetically, or both, as in the case of the negative index of refraction material.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

It is claimed that:

1. A steerable electromagnetic beam-former, comprising:
at least one rod of a plurality of rods having a refractive index, a magnetic permeability, and an electric permittivity wherein its magnetic permeability is influenced by magnetic field;
at least one linear ferromagnetic rod of a plurality of rods wherein the magnetic field of the at least one linear ferromagnetic rod is varied;
an electromagnetic beam traversing the rod wherein the direction of the beam is controlled by the magnetic permeability of the at least one of the plurality of rods;
a Bessel beam formed by influence of the variable magnetic field on the magnetic permeability of the plurality of rods; and
a steerable Bessel beam wherein varying the magnetic field of the at least one linear ferromagnetic rod influences the Bessel beam in a particular direction.

2. The apparatus of claim 1, further comprising:
the at least one linear ferromagnetic rod comprising a rod of soft iron.

3. The apparatus in claim 1, further comprising:
the rod comprising a photonic crystal wherein the photonic crystal is a Bloch-mode photonic crystal composed of parallel rods.

4. The apparatus in claim 1, further comprising:
the plurality of rods comprising meta-material.

5. The apparatus in claim 3, further comprising:
the photonic crystal operating in the microwave range; and
the photonic crystal having a negative refractive index for the beam-former.

6. The apparatus in claim 3, further comprising:
the photonic crystal operating in the microwave range; and
the photonic crystal having a positive refractive index for the beam-former.

7. The apparatus in claim 3, further comprising:
the photonic crystal operating in the microwave range; and
the photonic crystal having the at least one ferromagnetic control rod which controls the magnetic field in the photonic crystal wherein the at least one ferromagnetic control rod is in turn controlled by a controllable external current.

8. The apparatus in claim 3, further comprising:
the photonic crystal operating in the microwave range; and
the non-ferromagnetic rods comprising a conductive metal.

9. The apparatus in claim 3, further comprising:
the photonic crystal operating in the microwave range; and
the non-ferromagnetic rods comprising a dielectric material.

10. The apparatus in claim 3, further comprising:
an external controller, wherein the currents applied to the ferromagnetic rods may be controlled as to amplitude, frequency and phase.

\* \* \* \* \*